United States Patent [19]

Whitt

[11] 4,377,161

[45] Mar. 22, 1983

[54] SURGICAL BREATHING APPARATUS

[76] Inventor: Everett D. Whitt, 3504 Rivercrest Dr., Columbus, Ohio 43223

[21] Appl. No.: 273,500

[22] Filed: Jun. 15, 1981

[51] Int. Cl.³ .............................................. A61M 16/00
[52] U.S. Cl. ........................... 128/200.24; 128/204.18; 128/205.26
[58] Field of Search ...................... 128/200.24, 204.18, 128/205.26

[56] References Cited

U.S. PATENT DOCUMENTS

| | | | |
|---|---|---|---|
| 2,290,437 | 7/1942 | Kilgore et al. | 128/200.24 |
| 3,530,515 | 9/1970 | Jacoby | 128/205.26 |
| 4,223,669 | 9/1980 | Morledge | 128/205.26 |
| 4,321,917 | 3/1982 | Campbell | 128/205.26 |

FOREIGN PATENT DOCUMENTS 107372  5/1939  Australia ........................ 128/205.26

Primary Examiner—Henry J. Recla
Attorney, Agent, or Firm—Robert B. Watkins

[57] ABSTRACT

An apparatus to assist patient breathing during surgical procedures which include a patient on an operating table. The apparatus includes a member supporting a frame over an operating table. The frame is constructed and formed to support the surgical draperies and to supply oxygen-enriched air very close to the vicinity of the nose of the patient without contacting the patient.

6 Claims, 5 Drawing Figures

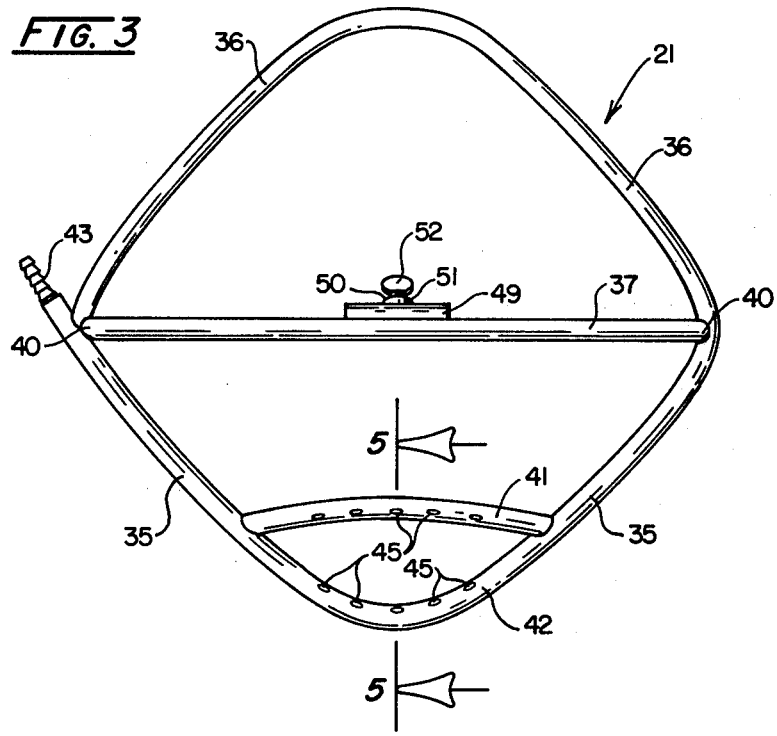
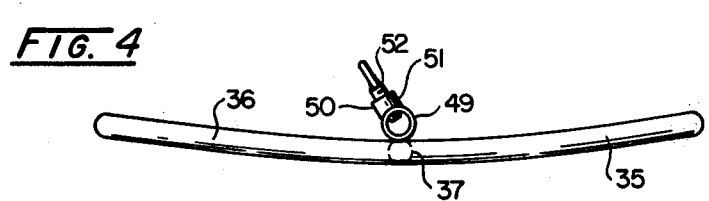
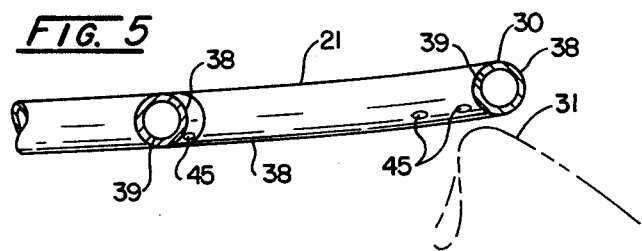

SURGICAL BREATHING APPARATUS

SUMMARY OF THE DISCLOSURE

This invention relates to a surgical breathing apparatus and more particularly to a device for providing breathing gas such as oxygen to a patient undergoing surgery on an operating table.

Briefly and in summary, the invention is an apparatus to assist patient breathing during surgical procedures on an operating table, and it comprises (a) a frame of hollow members having a lateral member connected to an surrounding or encircling perimeter member, with the perimeter member formed with a bridge portion in general conformity to the nose of a patient and projecting generally in a plane parallel to the surface of the face and torso of the patient on the operating table, with the hollow members being formed as an enclosed conduit having at least one inlet aperture for the admission of breathing gas and at least one outlet aperture in the bridge portion for the discharge of breathing gas; and (b) a support member adjustably connected to the frame having clamping means to support the apparatus on the operating table.

Although various kinds of apparatus have been provided in the past for the purpose of conveniently providing breathing gas, primarily oxygen, to patients in medical procedures, satisfactory and well accepted devices have not generally been in use. This is particularly true in connection with those surgical procedures which are done under local anesthetic. In these circumstances, the patient remains conscious and mentally alert while the procedure takes place upon an organ or part of the body which has been anesthetized in an area local to the site of the surgery.

One typical example is the kind of operations that are performed on the head, face or eyes. For instance, in eye surgery it is common to locally anesthetize the face, head and eyes. The patient lies prone upon his/her back with sterilized sheets covering all parts of the body except the eye area. A breathing gas such as air and/or oxygen is presented beneath the sheets in the general vicinity of the patient's nose. This has commonly been done by taping a flexible tube to the patient in or near the patient's nostrils, and sending oxygen through the tube.

In the past, there have been problems with these techniques in that some patients develop a feeling of claustrophobia with sensations of smothering. This leads to nausia, vomiting and at the least, restlessness which disrupts the operations.

Ophthalmolic surgery is one kind of surgery where the movements and actions of the surgical team is very delicate. If the patient moves, the consequences can be serious. However, due to the lack of oxygen-enriched air and the feeling of suffocation, the patient may become restless and move about at a time when the incision has already been made. There is an increase in the orbital venous pressure associated with the respiratory embarrassment problem. As this sequence of events occurs, the vitreous could be lost and intraocular bleeding is enhanced thus creating a situation where the success of the intended ocular surgery is compromised and even the loss of the eye could occur. Patients have, for many years, feared this situation and dread it more than the surgery itself. The feeling of suffocation is made worse by the pressure and blockage by the nasal oxygen tube commonly strapped close to the patient's nose in prior art practice, since it does not always stay in place. The nasal tubes and drapes may cover the nose and mouth compounding the difficulty. This situation occurs in all surgery performed under local and standby anesthesia.

In this invention, a new and novel oxygen delivery system has been created, which alleviates these problems.

This invention carries out the object of providing breathing gas adjacent to the nostrils of the patient without contact on the face of the patient. The gas is supplied in an enclosed area created by the surgical sheets and covers the face of the patient. Since patients come in various sizes and shapes, their faces, noses and torsos are individually adjusted to and accommodated by the apparatus. This is accomplished by providing, in the first instance, a general configuration with compliments, in general, the human configuration. Secondly, this is accomplished by providing means for adjusting the position of the apparatus relative to the patient on the operating table. These adjustment means include pivotal connections at a support means which is pivotally and slidingly engaged in a bracket on the side of the operating table. The bracket on the side of the operating table is conventional and readily found in the operating room situation.

In the use of the apparatus of this invention, all of the patients have been comfortable. A large area of constantly pooled oxygen-enriched air comes from openings in the apparatus and enters the vicinity of the nose and mouth. The elliptical tubular unit makes a desirable platform, keeping all of the surgical drapes and sheets from encroaching upon the nose and mouth which eliminates the patient's feeling of suffocation with all of its undesirable, psychological affects. Because the oxygen-enriched air is supplied in close proximity to the nostrils of the particular patient, the air is cool and refreshing and is constantly replenished. Head and neck movements are not restricted, when permitted during the operating procedures.

Some of the approaches of the prior art and the problems at which this invention is directed will be found in U.S. Pat. Nos. 2,499,650, 3,530,515, and 3,859,993.

U.S. Pat. No. 3,530,513 discloses the unrefined approach of providing breathing gas by attaching a flexible hose in the vicinity of the patient's nose. Of course, such a hose is subject to flexible distortions and movements which cannot be observed when the surgical drapes are in place. This creates uncertainties and problems as previously described when patients are restless.

U.S. Pat. No. 3,859,993 shows an apparatus which supplies oxygen from a relatively rigid and unadjustable framework which is located away from the face, nostrils and torso of the patient.

Further object of the features of this invention will be apparent from the drawings and detailed description which follows.

DESCRIPTION OF THE DRAWINGS

FIG. 3 is a planned view of the frame member of the apparatus of this invention viewed from beneath normal operative position.

FIG. 4 is a side view of the frame member of this invention.

FIG. 5 is an enlarged section view of a portion of the frame member of the apparatus of this invention, taken along the line 5—5 of FIG. 3.

DETAILED DESCRIPTION OF THE INVENTION

Figure 1:
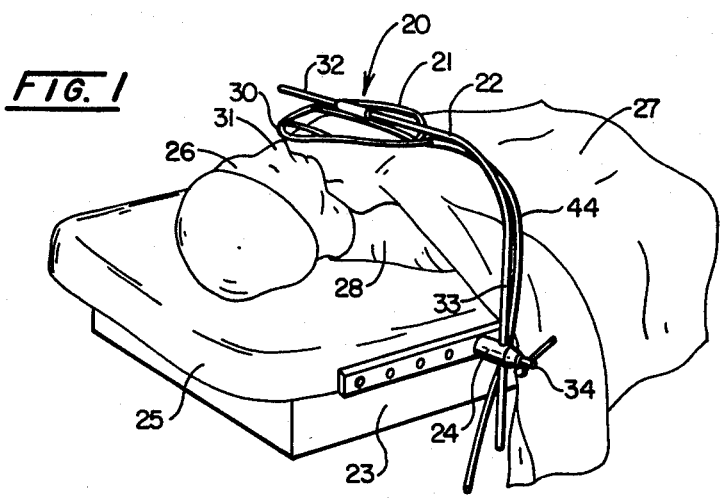
FIG. 1 is a perspective view of the apparatus of this invention in operative position above and near a patient on an operating table.
Figure 2:
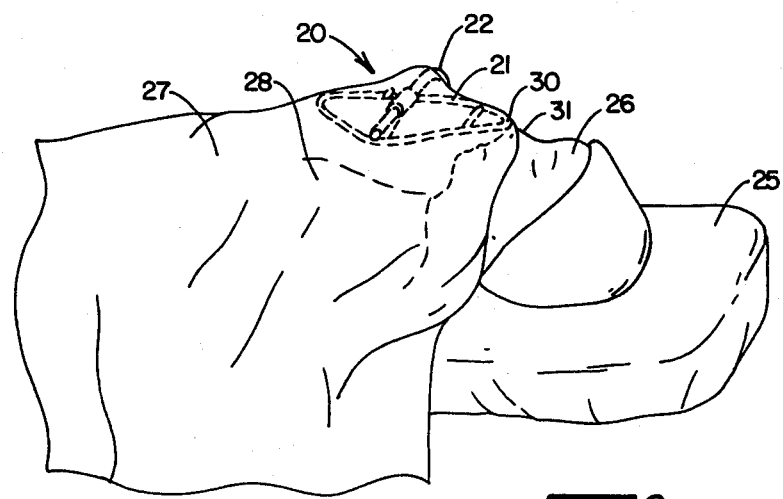
FIG. 2 is a perspective view taken from the side, showing the apparatus of this invention in position over a patient with the surgical drapes/sheets in position on the apparatus.

Referring to FIGS. 1 and 2, the apparatus 20 includes a frame 21 positioned on a support member 22 which is formed over the side of an operating table 23 and down into a bracket 24. The operating table 23 supports a mattress 25 on which a patient 26 reclines. Surgical drapes 27 cover a torso portion 28 of the patient 26. A head end 30 of the frame 21 is adjusted to a position in close proximity to the nose 31 of the patient 26.

Referring to FIG. 3, the frame 21 comprises a head end portion 35 and a lower end portion 36 fastened on opposite sides of a lateral member 37. Lateral member 37 is positioned generally across the frame and perpendicular to the longitudinal direction between the head end portion 35 and the lower end portion 36. The head end portion 35 and the lower end portion 36 generally surround or encircle the lateral member 37 and form a surrounding or encircling perimeter configuration of the frame 21.

As also seen in FIG. 5, the frame 21 is comprised of hollow, tubular material having outer surfaces 38 and inner surfaces 39.

In the preferred embodiment shown, the encircling perimeter comprises opposing V-formed head end and lower end members, 35 and 36 consecutively, which intersect and connect to the lateral members at support points 40 at opposite ends. A cross frame section 41 is connected laterally near an apex 42 of the head end portion 35. At one side a hose fitting 43 is fastened into the end of the head end portion 35. The hose fitting 43 is conventional in construction to receive and connect to a flexible, surgical grade plastic or rubber tubing 44 (see FIG. 1) through which can be supplied oxygen-enriched air or other breathing gas.

Apertures 45 provide communication between the inside and the outside of the frame. The number of apertures 45 is not critical. Obviously, at least one is necessary and it has been found between 10 and 20 is very effective. The apertures 45 are located generally in close proximity to the position of the nose 31 of the patient 26 and in the preferred embodiment shown are positioned with their axes directed toward the nostril of the patient 26. These positions, and the general position and formation of the frame 21 bring the most optimum communication of breathing gas to the patient 26 without any contact with the body of the patient.

A sleeve 49 is fastened to lateral member 37. An adjustment means 50, includes a boss 51 which is provided with a threaded bore to receive a locking thumb screw 52 which passes through the boss 51 and protrudes for contact when the support 22 is passed through the sleeve 49.

The frame and apparatus may be connected together by conventional, suitable means such as welding or soldering as the situation requires.

Support member 22 comprises a generally horizontal portion 32 and a vertical portion 33. The vertical portion 33 passes through the bracket 24 and is clamped with a lockarm screw 34.

One of the features of this invention is the simplicity of its operation in which the lockarm screw 34 is loosened and the support member 22 swung out of the way during the early preparation of the patient 26 for surgery. After the patient is in place, the support 22 is swung back into position across, above and close to the torso of the patient 26, where it is locked in position by tightening lockarm screw 34. Adjustment as to height and lateral position are available. The attitude and position of the frame is then adjusted by sliding and rotating the sleeve 49 on the support 22. When the best position is achieved, the frame is locked into position with the thumb screw 52.

The configuration and construction of the frame 21 with the position of the apertures 45 make it possible to create a pocket of cool oxygen-enriched air directly at the nostrils of the patient without ever touching the patient in any way. The patient therefore has no feeling of claustrophobia or suffocation.

Oxygen-enriched air is supplied through the tubing 44 into the frame 21 at the tube fitting 43 where it passes immediately to the vicinity of the head end portion 35 and is emitted from the apertures 45. The downwardly directed apertures convergently direct the breathing gas to the optimum position for the patients and the surgical procedures. Because of the simplicity of the apparatus the objects of the invention are surprisingly achieved. At the same time, in the event of an untoward situation developing during the operating procedures in which the surgical breathing apparatus is in the way, it may be quickly and easily removed by loosening the lock arm screw 34 without affecting sterilization or draping.

The above described apparatus provides constantly changing pools of cool oxygen-enriched air at the area of the nose and mouth. The oxygen is delivered from the operating room intake valve and passed through a sterile water container before it enters the plastic tube connected to the frame. The formation of the frame allows the frame to be very close to the patient, but keeps the drapes from covering the nose and mouth to avoid giving the patient a feeling of suffocation.

The instrument can be used on each side of the operating table since the lockarm screw 34 is conventional, standard equipment on surgical operating tables and can be used on either side.

It is herein understood that although the present invention has been specifically disclosed with the preferred embodiments and examples, modifications and variations of the concept herein disclosed may be resorted to by those skilled in the art. Such modifications and variations are considered to be within the scope of the invention and the appended claims.

What is claimed is:

1. An apparatus to assist patient breathing during surgical procedures on an operating table comprising:
   (a) a frame of hollow members having a lateral member connected to surrounding perimeter members, the perimeter members formed into a rectangle-like configuration having rounded corners with said lateral member being connected between two opposing diagonal corners and one of the remaining corners defining a head end portion adapted to overlie the nose of the patient and project generally in a plane parallel to the surface of the face and torso of the patient on the operating table, the surrounding hollow members being formed as an enclosed conduit having at least one inlet aperture for the admission of breathing gas and at least one outlet aperture in the head end portion; and (b) a support member adjustably connected to the frame and having clamping means to support the apparatus on the operating table.

2. A breathing apparatus according to claim 1 wherein the frame is made of tubing.

3. A breathing apparatus according to claim 1 wherein the support member engages the lateral member.

4. A breathing apparatus according to claim 2 wherein the head end portion includes a hollow complementary cross frame section diagonally connected across said corner defining said head portion, and both the head end portion and the cross frame section have at least one outlet aperture.

5. A breathing apparatus according to claim 4 wherein the outlet apertures are directed downward.

6. A breathing apparatus according to claim 4 wherein the outlet apertures are convergently directed in the vicinity of the position of the nose of the patient.

* * * * *